United States Patent
Lee et al.

(10) Patent No.: US 9,259,210 B2
(45) Date of Patent: Feb. 16, 2016

(54) TISSUE SAMPLING TOOL

(75) Inventors: Men-Jean Lee, Irvington, NY (US); Luca Lambertini, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 1042 days.

(21) Appl. No.: 13/101,797

(22) Filed: May 5, 2011

(65) Prior Publication Data

US 2011/0275955 A1 Nov. 10, 2011

Related U.S. Application Data

(60) Provisional application No. 61/332,082, filed on May 6, 2010.

(51) Int. Cl.
| | |
|---|---|
| *A61B 10/00* | (2006.01) |
| *A61B 10/02* | (2006.01) |
| *A61B 17/3205* | (2006.01) |
| *G01N 1/31* | (2006.01) |
| *G01N 1/36* | (2006.01) |

(52) U.S. Cl.
CPC ....... *A61B 10/0233* (2013.01); *A61B 17/32053* (2013.01); *G01N 1/31* (2013.01); *G01N 1/36* (2013.01)

(58) Field of Classification Search
CPC ....................................................... A61B 10/02
USPC ......................................... 600/562, 564, 567
See application file for complete search history.

(56) References Cited

U.S. PATENT DOCUMENTS

| | | | |
|---|---|---|---|
| 2,818,852 A | | 1/1958 | Kugler et al. |
| 5,133,360 A | * | 7/1992 | Spears .......................... 600/567 |
| 5,195,988 A | * | 3/1993 | Haaga ............................ 604/265 |
| 5,507,765 A | | 4/1996 | Mott |
| 5,827,199 A | | 10/1998 | Alexander |
| 6,792,305 B2 | * | 9/2004 | Rastorgoueff et al. ........ 600/547 |
| 2004/0167429 A1 | | 8/2004 | Roshdieh et al. |
| 2005/0256425 A1 | * | 11/2005 | Prusiner ........................ 600/567 |
| 2007/0249960 A1 | * | 10/2007 | Williamson ................... 600/564 |
| 2008/0039740 A1 | | 2/2008 | Chiu et al. |
| 2009/0018467 A1 | * | 1/2009 | Chiu et al. .................... 600/562 |
| 2009/0198184 A1 | * | 8/2009 | Martin et al. ................. 604/151 |
| 2010/0210967 A1 | * | 8/2010 | Sjunnesson et al. .......... 600/567 |

* cited by examiner

*Primary Examiner* — Sean Dougherty
*Assistant Examiner* — Daniel Cerioni
(74) *Attorney, Agent, or Firm* — Leason Ellis LLP

(57) ABSTRACT

A sampling tool for isolating and collecting a tissue biopsy includes a hollow sampling cylinder that includes a first end and an opposing second end. The first end being a sharpened, annular cutting edge and a central bore extending completely from the first end to the second end. The sampling tool also includes a plunger having a first end and a second end. The plunger includes an air evacuation feature in the form of an air evacuation channel that extends from one end of the plunger to the other end and is open at both ends. The sampling tool has particular utility in isolating and collecting cylindrical core placental biopsies of a standardized size that can be used for multiple downstream applications, including the sampling of other harvested solid, soft-tissue organs such as brain, liver, kidney, and spleen.

7 Claims, 15 Drawing Sheets

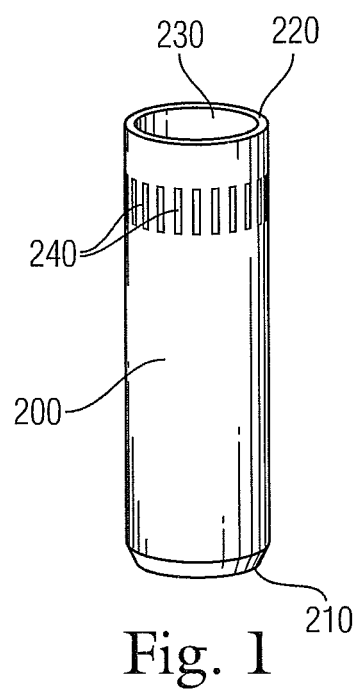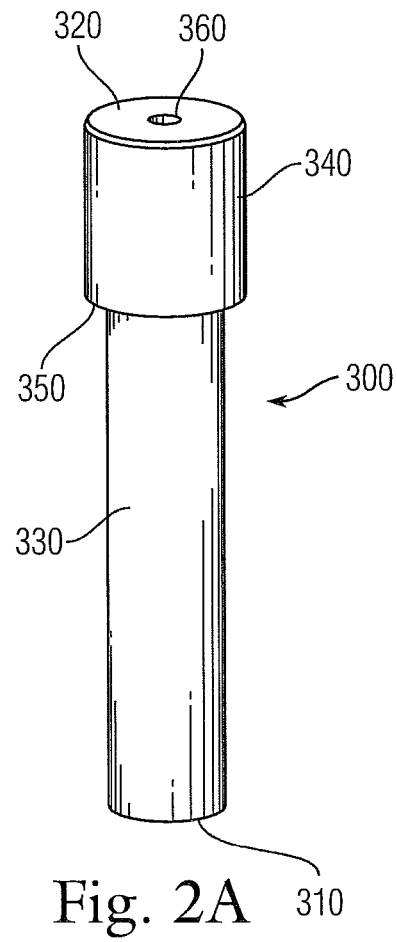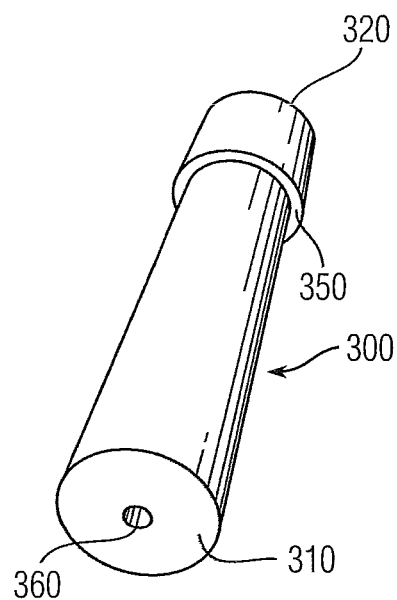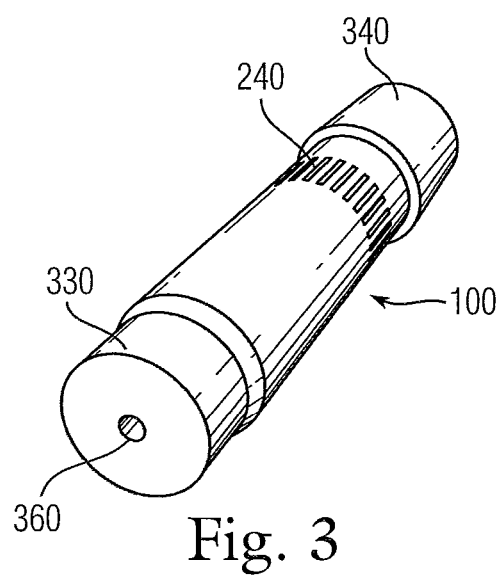
Fig. 1
Fig. 2A
Fig. 2B
Fig. 3

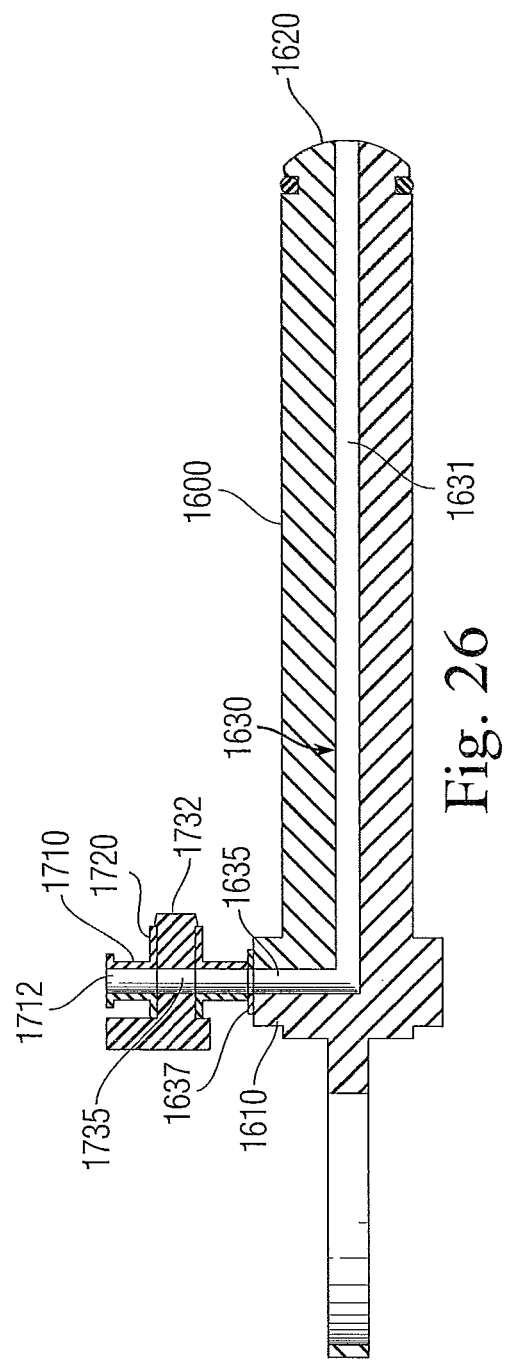
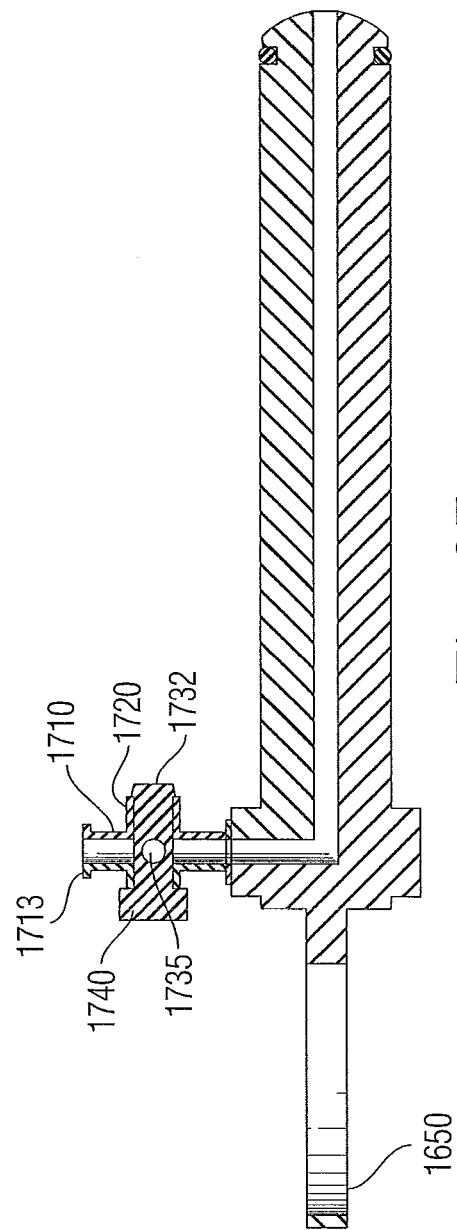

TISSUE SAMPLING TOOL

CROSS REFERENCE TO RELATED APPLICATION

The present application claims the benefit of U.S. patent application Ser. No. 61/332,082, filed May 6, 2010, which is hereby incorporated by reference in its entirety.

TECHNICAL FIELD

The present invention relates to a tool for isolating and processing tissue specimens and in particular, to a sampling tool that has specific utility in performing standardized full-thickness biopsies of tissue, such as placenta tissue.

BACKGROUND

In many different settings and applications, there is a need to collect tissue specimens in larger quantities greater than available by fine-needle biopsy. Examples are the sampling of discarded tissues such as the placenta and tumors, but also, other solid organs isolated in the framework of a human surgical excision or autopsy or animal necropsy for clinical and/or research purposes (including tumor banks and registries).

Using the placenta as an example for an organ of interest, it governs the nutrient uptake, waste elimination, and gas exchange of the developing fetus via maternal blood supply. The whole placenta has a thickness of about 2.0 cm-2.5 cm (¾"-1") and is oriented by a maternal side and fetal side, with different layers that has specific associated functions. This temporary organ is of overwhelmingly fetal origin; however, at term, there is a thin layer on the maternal side that is an adherent layer of maternal tissue known as the decidua which was previously attached to the uterus prior to birth of the fetus. Furthermore, the blood that peruses the placenta is of maternal origin. This makes of the placenta a unique source of fetal tissue for the study of fetal development. The placenta is invariably discarded following the birth of an infant. The human placenta has a spongy, friable, and gelatinous consistency that makes it very difficult to handle. These characteristics make the consistent and reproducible excision of placental tissue particularly challenging.

Currently, placenta sampling is routinely carried out by using sterile disposable scalpels and forceps to perform full thickness sections that produce large, irregular cubically shaped biopsies. This method is tedious and bloody, thus presenting a safety issue for the operator/user collecting the tissue sample. Furthermore, the use of the scalpel does not allow for procedural standardization, and exposes the personnel to the risk of laceration by the protruding nature of scalpel blade in the setting of the slippery nature of the tissue and exposure to abundant maternal blood percolating through the incised placenta that obstructs the operator's view of the incision site. Use of a scalpel places the operator at risk for puncture and laceration with exposure to potentially infectious blood products.

SUMMARY

In one embodiment of the present invention, a sampling tool for isolating and collecting a tissue biopsy includes a hollow sampling cylinder that has a first end and an opposing second end. The first end is an annular, sharpened cutting edge (similar to a cookie-cutter) and a central bore extending completely from the first end to the second end. An outer surface of the sampling cylinder includes a modified gripping surface. The sampling tool also includes a plunger that has a first end and a second end. The plunger includes a shaft portion that terminates in the first end. The plunger has a handle portion at the second end that has greater dimensions than the shaft portion. The plunger carries an air evacuation channel made of a central hollow bore of about 0.3 cm of diameter (⅛") running from the first to the second end in order to allow for the plunger to be inserted in the sampling cylinder to reach the surface of the biopsied tissue. By obliterating the second end of the air evacuation channel with a finger the user can create a close chamber that allows for generating the suction power needed for the retrieval of the excised tissue by simply pulling the plunger toward the second end of the sampling cylinder. In one embodiment, the sampling cylinder has a length of between about 5 cm to about 10 cm and preferably at least about 7.5 cm (~3") and a diameter of about 1.5 cm (⅝") (e.g., a diameter in a range of about 1-2 cm). The sampling tool has particular utility in isolating and collecting cylindrical core placental biopsies of a replicated size that can be used for multiple downstream applications, including sampling of other harvested solid, soft-tissue organs such as brain, liver, kidney, spleen, etc.

A method of isolating a core placental biopsy of a standardized size includes the steps of: 1) carefully placing the placenta on a hard surface with the fetal side exposed; 2) gently pressing the sharpened cutting edge of the hollow sampling cylinder into the exposed placental side while contemporaneously rotating the tool with clockwise and counterclockwise twisting motion and vice versa by operating with thumb and index fingers positioned over the gripping surface; 3) once the tool penetrates through all placental layers, the plunger is inserted to reach the top of the biopsied tissue, the top of the air evacuation channel is obliterated by using the thumb finger while grabbing the plunger handle with the index and $2^{nd}$ finger; 4) applying a gentle suction by partially extracting the plunger; 5) extruding the tissue to the desired processing length by expelling the biopsy from the sampling cylinder by pressing the plunger to expose its end which also protects the sharp edge of the blade. The sampling cylinder is designed to have a sharpened scalpel-like edge that allows ease of cutting through the tissue layers to avoid compression and displacement of the extracted tissue, thus compromising the tissue collection. The tool blade is also designed to prevent uneven superficial incisions of the tissue that could lead to widespread lacerations of the placental membranes. The circular design of the cutting edge is a safety feature to minimize puncture wounds to the operator.

These and other aspects, features and advantages shall be apparent from the accompanying Drawings and description of certain embodiments of the invention.

BRIEF DESCRIPTION OF THE DRAWINGS

FIG. 1 is a perspective view of a sampling cylinder of a sampling tool according to a first embodiment;

FIGS. 2A and B are magnified perspective end views of the plunger of the sampling tool;

FIG. 3 is a perspective view of the sampling tool in an assembled condition;

FIG. 26 is a cross-sectional view of the plunger of FIG. 24 in the open position; and FIG. 27 is a cross-sectional view of the plunger of FIG. 25 in the closed position.

DETAILED DESCRIPTION OF CERTAIN EMBODIMENTS OF THE INVENTION

Figure 4A:
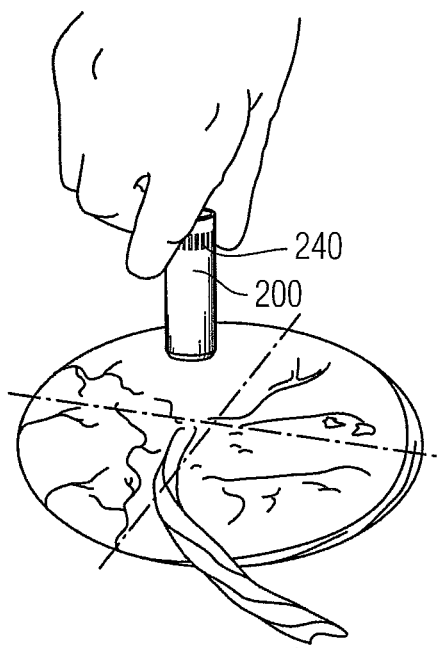
FIG. 4A is a perspective view showing a first step in collecting a sample of placenta tissue showing the sampling cylinder prior to contact with the placental tissue.

In terms of collection of placenta, the collection should be such to allow: (1) the collection of abundant fresh tissue to conduct the broadest possible set of clinical/experimental tests; (2) collect aliquots of tissue of a consistent sample size; and (3) preserve the organ integrity for downstream clinical pathological investigation. The present invention achieves these objectives.

The usual term placenta is shaped in the form of a disk of about 22 cm (8 and ½") in diameter and about 2.0-2.5 cm (¾"-1") thick. Placentas generally weigh approximately about 470 g (1 lb). In order to collect sufficient tissue for research/clinical studies, the best approach is that of sectioning full-thickness cylindrical areas through the placental disk, midway between the umbilical cord insertion site and the lateral margins of the placenta.

The whole placenta has a thickness that can reach a maximum of nearly about 2.5 cm (1") and the current scientific standard is to collect full-thickness transversal placenta sectional (from fetal to maternal side). This approach allow for isolating all placenta layers for downstream analyses. The structural dynamics of the placental tissue greatly support two principal features for the sampling tool: a cylindrical shape with a diameter between about 1 cm to 2 cm and preferably, about 1.5 cm (⅝") and a height of between about 5 cm to about 10 cm and preferably, at least about 7.5 cm (3") to allow for aspiration of the tissue core into the internal chamber of the sampling tool and provide with enough additional handling surface for operator safety.

As shown in FIGS. 1-3, a sampling tool 100 according to a first embodiment of the present invention includes a sampling cylinder 200 and a plunger 300 that is configured to be received within the sampling cylinder 200. The sampling cylinder 200 is an elongated hollow structure that has a first end 210 and an opposing second end 220 and a bore 230 that extends there from the first end 210 to the second end 220. In the illustrated embodiment, the cylinder 200 has a cylindrical shape and the first end 210 represents a specially designed and sharpened cutting edge 210. This sharpened first end 210 is defined by an edge (e.g., a beveled edge) that has scalpel-like sharpness (tapered cutting edge or blade) which allows sampling of the tissue (e.g., placenta) without applying undue pressure on the tissue that results in lateral displacement of the spongy and friable tissue. The opposite second end 220 can be a flat edge since it is a non-cutting edge.

In order to permit the user to hold and manipulate the sampling cylinder 200 during the procedure, the sampling cylinder 200 preferably includes a modified surface 240 that acts as a gripping surface. In the illustrated embodiment, the modified surface 240 is in the form of a plurality of grip tabs or pads 240 that are arranged circumferentially about the outer surface of the sampling cylinder 200. The grip pads 240 are located proximate the second end 220. It will be appreciated that the modified surface 240 can take other forms including a continuous grip band that extends around the complete circumference of the outer surface of the sampling cylinder 200.

The sampling cylinder 200 is formed of a rigid, robust material, such as a metal. The material used to make the sampling cylinder 200 is preferably autoclavable to maintain sterility.

The plunger 300 is an elongated body that has a first end 310 and an opposing second end 320. The plunger 300 is configured to be intimately received within the bore 230 of the sampling cylinder 200. The plunger 300 has a shaft portion 330 and a stop/handle portion 340. Thus, the shape and size of the shaft portion 330 is selected to be received within the bore 230 of the sampling cylinder 200 fitting tightly as a syringe plunger. As a result, in the illustrated embodiment, the shaft portion 330 has a cylindrical shape with the outer diameter of the shaft portion 330 being about equal to the diameter of the bore 230. The handle portion 340 terminates at the second end 320 and the shaft portion 330 terminates at the first end 310. The handle portion 340 has increased dimensions relative to the shaft portion 330 and therefore, a shoulder 350 is formed between the shaft portion 330 and the handle portion 340. The illustrated handle portion 340 has a cylindrical shape with the shoulder 350 having an annular shape.

The shaft portion 330 includes a vent (air evacuation channel) feature 360 formed therein to allow for the evacuation of air as the sampling procedure is performed. In the illustrated embodiment, the vent feature 360 is in the form of a bore or opening formed in the shaft portion 330 and extending along the length of the shaft portion 330 and the handle portion 340 that generates an air evacuation channel. The vent 360 is open along the first end 310 through the shaft 330 to the second end 320 and comes in the form of a circular shaped bore of about 0.3 cm (⅛") in diameter. The vent 360 permits air to flow through the vent channel for evacuation of the air as the plunger 300 is received within the bore 230 and comes into contact with the tissue sample. In the illustrated embodiment, the plunger 300 is a hollow member and the vent 360 is an opening that forms an entrance to the hollow interior.

The plunger of the present invention, including plunger 300, is thus cannulated to allow air to be vented through the plunger as the plunger is advanced into the cutter. This venting is necessary so that the advancement of the plunger will not displace the tissue from the cutting cylinder (tube). The air being vented may possible have blood or other bodily fluids in with it and for this reason, the venting hold and/or porting directs the fluid away from the technician, thus reducing the possibility of contamination to the technician. As described herein, the next step of the procedure is to have the plunger reverse its direction to facilitate the lifting and/or advancement of the sample tissue into the cylinder. To accomplish this, a partial vacuum has to be formed between the face of the plunger and the tissue sample. To allow this to happen, the cannulated vent hole must be sealed. The sealing of the vent hole can be accomplished in at least two ways which are described herein. This first way is for the technician to put his or her finger over the vent hole, while the second way is for the technician to manually actuate a valve specifically designed to seal off the air producing the suction as the plunger is distracted from the sample site. The valve can thus be designed so that when the plunger is advanced forward toward the tissue, the valve is open to permit air to flow completely through the vent passage. However, when the plunger is moved in the opposite direction so as to remove the plunger from the tissue site, the valve is closed so as to seal off the air within the vent passage.

As mentioned, the valve can be of a manually actuated type and therefore, the technician can manually manipulate the valve, as by an actuator or control element or the like, so as to move the valve between the open and closed positions.

The length of the shaft portion 330 is such that when the plunger 300 is fully inserted into the sampling cylinder 200 and the handle portion 340 contacts the second end 220, the length of the shaft portion 330 extends beyond the sharpened first end 210 of the sampling cylinder 200. This length is approximately 2.5 cm (1") so that to guarantee the effective ejection of the sampled tissue from the sampling cylinder 200 while contemporaneously protecting the sharp edge of the sampling cylinder 210. This aspect is shown in FIG. 3. The shoulder 350 acts as a stop since it has a greater diameter than the second end 220 and therefore, limits the degree of travel of the plunger 300 within the bore 230 of the sampling cylinder 200. This ensures that when the plunger 300 is fully inserted into the bore 230, the sample specimen that is captured and held within the bore 230 is ejected.

The plunger 300 can be formed of any number of different materials, including but not limited to a metal or plastic.

Figure 6:
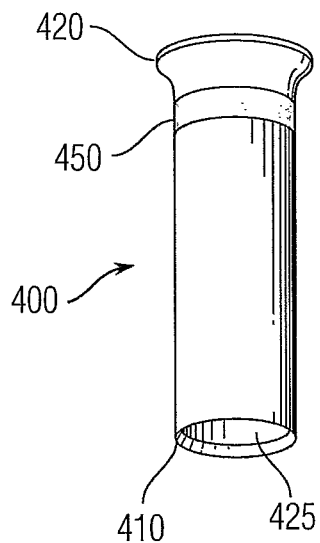
FIG. 6 is a side perspective view of a sampling cylinder according to a second embodiment.

FIG. 6 shows a sampling cylinder 400 according to a second embodiment. The sampling cylinder 400 is similar to the sampling cylinder 200 and is an elongated tube shaped structure that includes a first end 410 and an opposing second end 420 and a bore 425 extending from the first end 410 to the second end 420. The first end 410 is defined by a sharp edge (scalpel-like sharpness), while the second end 420 is an outwardly flared end. The second end 420 thus is in the form of a flange. A grip band 450 is provided along the outer surface of the sampling cylinder 400 and in the illustrated embodiment, the grip band 450 is a continuous annular shaped structure.

Figure 7:
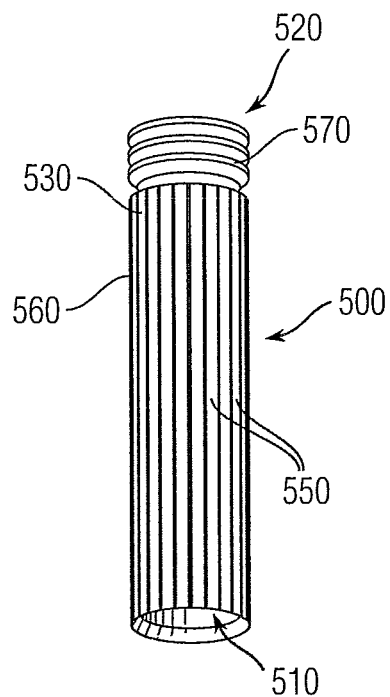
FIG. 7 is a side perspective view of a plunger according to a second embodiment.

FIG. 7 shows a plunger 500 according to a second embodiment. The plunger 500 is an elongated member with a first end 510 and an opposing second end 520. The first end 510 includes a bottom ejection surface, while the second end 520 is in the form of a top pushing surface. The plunger 500 includes an outer surface 530 and is shaped and sized to be received within the bore 425 of the cylinder 400. The plunger 500 has a shaft portion 560 (that terminates at the first end 510) and an end or handle portion 570 (that terminates at the second end 520) that is held by the user.

The plunger 500 includes a venting feature that is in the form of a plurality of air evacuation grooves 550 that are formed in the outer surface 530 and extend longitudinally along the length of the shaft portion. In the illustrated embodiment, the air evacuation grooves 550 are linear grooves that extend the entire length of the shaft portion.

As with the previous embodiment, the length of the shaft portion 560 is such that when the plunger 500 is inserted into the sampling cylinder 400, a length of the shaft portion 560 extends beyond the first end 410 of the sampling cylinder 400.

In one embodiment, the sampling cylinder 400 has an inner diameter of about 1 inch and a length of about 3 inches and the shaft portion 560 of the plunger 500 has an outer diameter of about 1 inch and a length of about 3.5 inches. The total length of the plunger 500 is thus greater than about 3.5 inches due to the length of the handle portion 570.

The method of using the sampling tool 100 is described below. A target tissue sample that is desired to be collected is identified. It will be appreciated that while the sampling tool 100 has particular utility in collecting placenta samples, the sampling tool 100 is not however limited to only collecting placenta tissue and instead the sampling tool 100 can be used to sample other types of tissue.

Figure 4B:
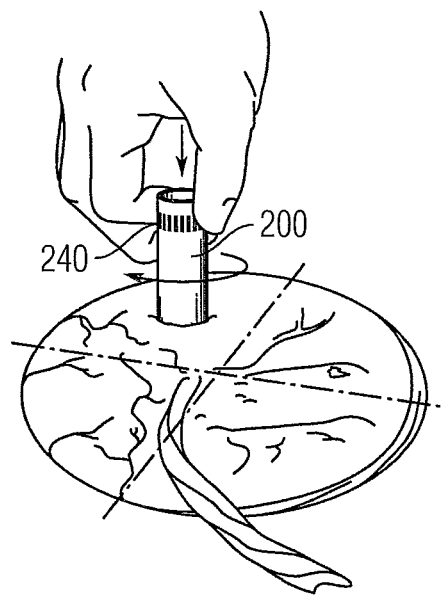
FIG. 4B is a perspective view showing a second step where the sampling cylinder is inserted into and through the placental tissue by means of a sharpened end of the plunger.
Figure 4C:
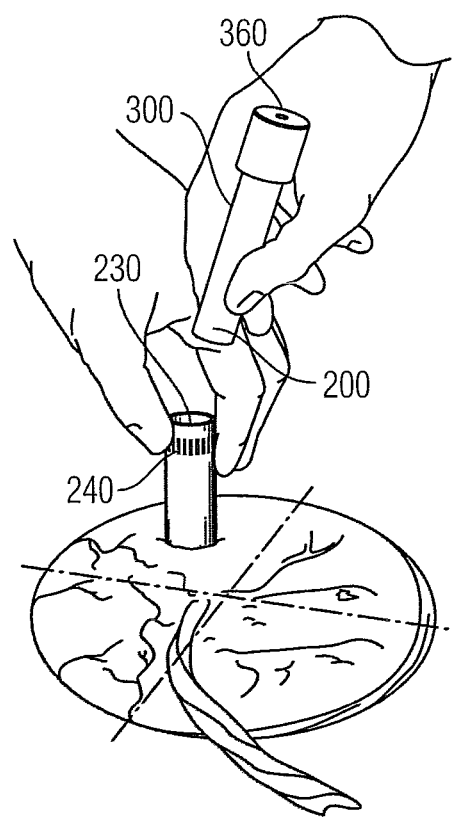
FIG. 4C is a perspective view showing a third step where the plunger is aligned with the sampling cylinder for insertion into the bore of the sampling cylinder.
Figure 4D:
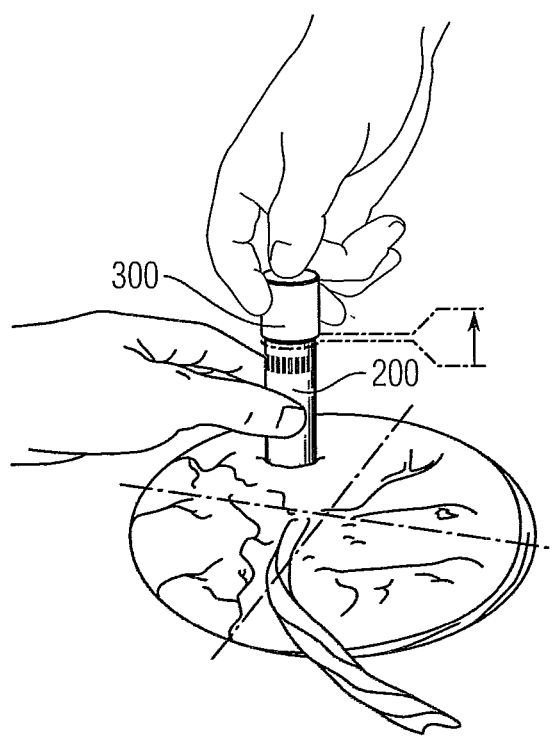
FIG. 4D is a perspective view of the biopsy retrieval with a thumb of a user placed over a plunger air evacuation channel coupled with the slight extraction of the plunger from the sampling cylinder to generate suction to hold the tissue inside the sampling cylinder while recovering the biopsy.
Figure 5A:
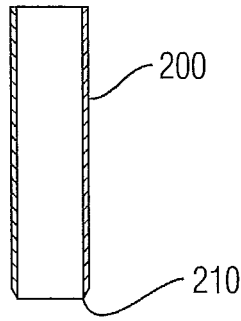
FIG. 5A is a cross-sectional view taken through the sampling cylinder.
Figure 5B:
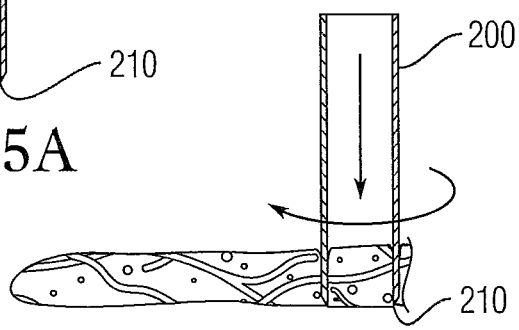
FIG. 5B is a cross-sectional view taken through the sampling cylinder and the placenta with the sampling cylinder being inserted through the placenta by means of both linear and rotational movement of the sampling cylinder.
Figure 5C:
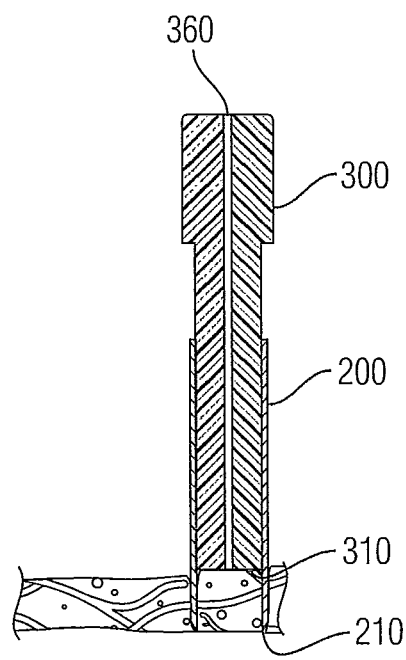
FIG. 5C is a cross-sectional view taken through the sampling cylinder, plunger and the placenta showing the plunger being inserted into the sampling cylinder and in contact with a top of the biopsy contained in the sampling cylinder.
Figure 5D:
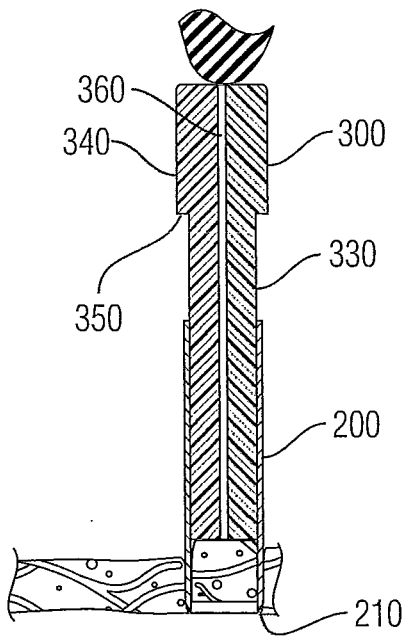
FIG. 5D is a cross-sectional view taken through the sampling cylinder and plunger with the plunger being moved slightly to retract the biopsied tissue within the cylinder under a vacuum, created in part by the user covering the plunger air evacuation channel, to retrieve the biopsied tissue.

The sampling cylinder 200 is used to isolate and collect cylindrically shaped core tissue biopsies of a standard size that can be used in multiple downstream applications. The first end 210 of the sampling cylinder 200, which represents the scalpel-sharp cutting edge, is gently pressed into the surface of the organ and twisted rotationally clockwise and counterclockwise, and vice versa, as shown and indicated by the directional arrows in FIG. 5B, by operating on the gripping surface 240 of the sampling cylinder with thumb and index fingers. By applying a constant, gentle and continuous pressure the sampling cylinder is then inserted into and all the way through the target tissue so as to isolate a full-thickness tissue sample (e.g., for placenta, an about 2.0-2.5 cm (¾"-1") thick cylindrical core biopsy). The scalpel-like sharpness of the first end 210 allows for easy sampling of organs like the placenta without applying undue pressure that would result in lateral displacement of tissue particularly in spongy or friable organs and provides safety to the user since excessive pressure on the cutting edge is not required to obtain the sample. The user grips the second end 220 of the sampling cylinder about the modified gripping surface 240 to perform the core sampling. FIGS. 4B and 5B show the above step being performed. FIGS. 4D, 5C and 5D show the removal of the tissue sample contained within the sampling cylinder 200.

Figure 5E:
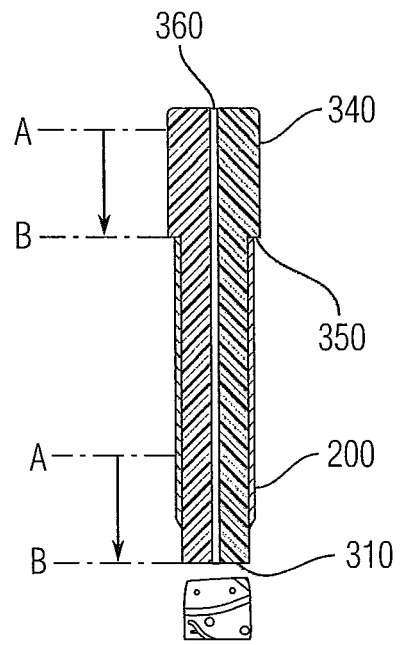
FIG. 5E is a cross-sectional view taken through the sampling cylinder and plunger with the plunger being fully inserted into the sampling cylinder for ejecting the tissue sample from the sampling cylinder.

As shown in FIGS. 5C-5E, once the core sample has been isolated within the first end 210 of the sampling cylinder 200, the user then inserts the first end 310 of the plunger 300 within the bore 230 of the sampling cylinder 200 making contact with the isolated biopsied tissue sample (FIG. 5C). The vent channel 360 evacuates the air trapped between the first end 310 of the plunger 300 and the tissue. Once the first end 310 of the plunger 300 reaches the tissue, the user places his or her thumb (or finger) on the vent channel opening 360 at the second end 320 of the plunger 300 (FIG. 5D). The vent channel 360 now closed, thereby forming a chamber, allows for generating suction by simply slowly extracting the plunger 300 from the sampling cylinder 200 by grabbing the plunger handle 340 between index and $2^{nd}$ finger. This system permits an easy retrieval of the biopsied tissue. Continued advancement of the shaft 330 within the bore 230 of the sampling cylinder 200 in a direction toward the end 210 of the cylinder 200 causes the sample to be ejected from the sampling cylinder 200 for further tissue processing as shown in FIG. 5E. The plunger 300 can be advanced until the shoulder 350 (stop feature) of the plunger 300 contacts the second end 220 of the sampling cylinder 200. This ensures that the tissue sample is ejected and the first sharp end 210 of the sampling cylinder 200 will be sheathed to prevent operator injury and laceration. In the case where several biopsies of the same organ are needed the procedure can be simply repeated by completely extracting the plunger 300 from the sampling cylinder 200 re-exposing the sampling cylinder sharp first end 210. This unique sampling approach promotes temporal efficiency and safety in the sampling of placenta tissue. The biopsied tissue held in the sampling cylinder exposes the maternal placental side which includes the decidua membrane of maternal origin. By holding the tool with one hand and exposing the maternal end of the biopsied tissue by slightly pressing the plunger into the sampling cylinder, the maternal decimal surface and be easily removed by using a pair of scissors to snip off the outer-most placenta layer of the biopsy before ejecting it from the tool for further processing.

Figure 8:
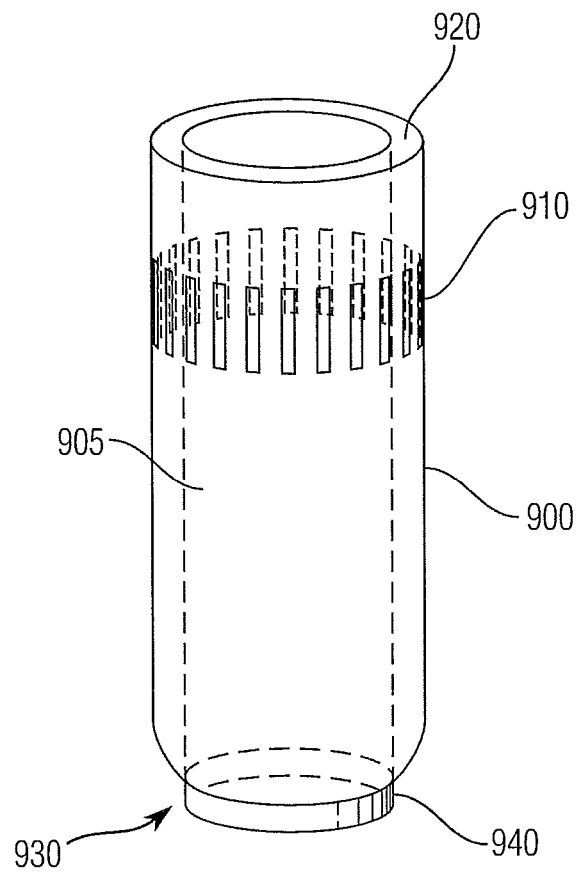
FIG. 8 is a side elevation view of a sampling cylinder according to a third embodiment.

FIG. 8 is a side elevation view of a sampling cylinder 900 according to another embodiment illustrating a cutting element according to a different embodiment. In this embodiment, the sampling cylinder 900 is a tool made of a cylindrically shaped plastic body with dimensions matching or similar to those of the sampling cylinders disclosed hereinbefore (e.g., metal tools). The sampling cylinder 900 includes a gripping surface 910 toward an end 920 opposite to a sampling end 930 and an annular blade 940 that is located at the sampling end 930. The annular blade 940 can be formed at the end using any number of different techniques including but not limited to a molding process. More particularly, the annular blade 940 (metal blade) can be molded in-situ when the plastic sampling cylinder 900 is formed.

The annular blade 940 preferably includes the same or similar characteristics of sharpness outlined for the metal tool embodiments described before. The thickness of the cylindrical wall 905 of the plastic cylinder 900 decreases at the sampling end 930 to allow for the tool to easily penetrate the tissue being biopsied.

Figure 9:
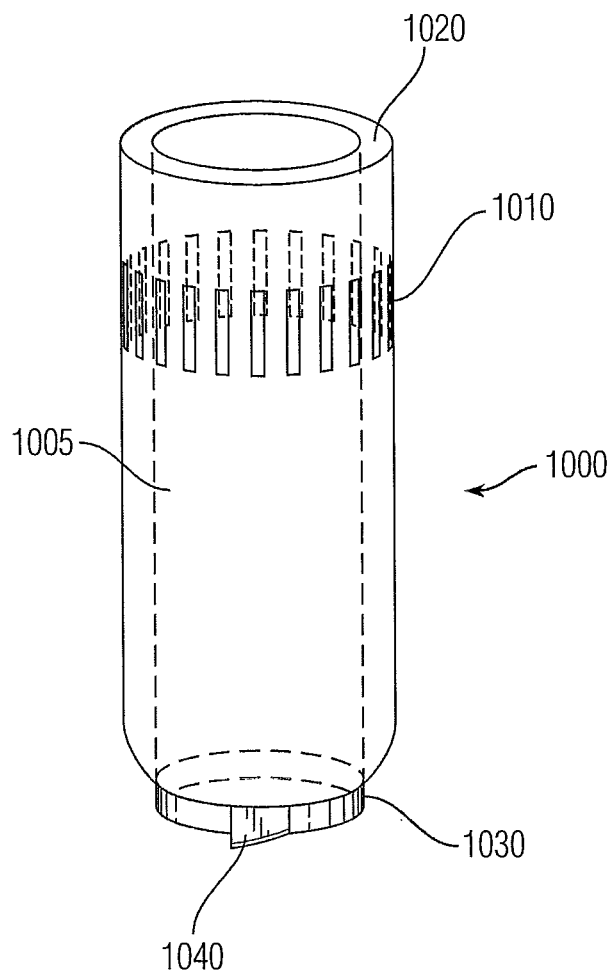
FIG. 9 is a side elevation view of a sampling cylinder according to a fourth embodiment.
Figure 12:
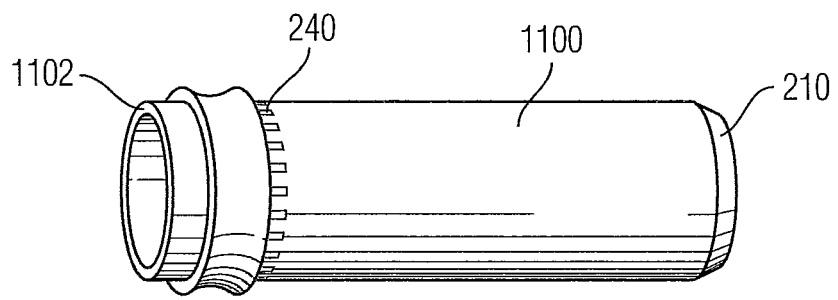
FIG. 12 is a perspective view of a sampling cylinder of the tool of FIG. 10.

FIG. 9 is a side elevation view of a sampling cylinder 1000 according to another embodiment illustrating a cutting element according to a different embodiment. The sampling cylinder 1000 entails a tool made of a cylindrically shaped plastic component of sizes that are similar or identical the sizes described hereinbefore with respect to the metal tools (metal sampling cylinders). The sampling cylinder 1000 includes a gripping surface 1010 toward an end 1020 opposite to a sampling end 1030 and a linear blade 1040 installed at the sampling end 1030. The linear blade 1040 preferably has similar or the same characteristics of sharpness as outlined hereinbefore with respect to the discussion of the metal sampling cylinders. The thickness of the wall 1005 of the plastic cylinder 1000 decreases at the sampling end 1030 to allow for the tool to easily penetrate the tissue being biopsied. As shown in FIG. 12, the linear blade 1040 does not extend around the complete circumference of the cylinder 1000 but rather is formed at a discrete location.

Figure 10:
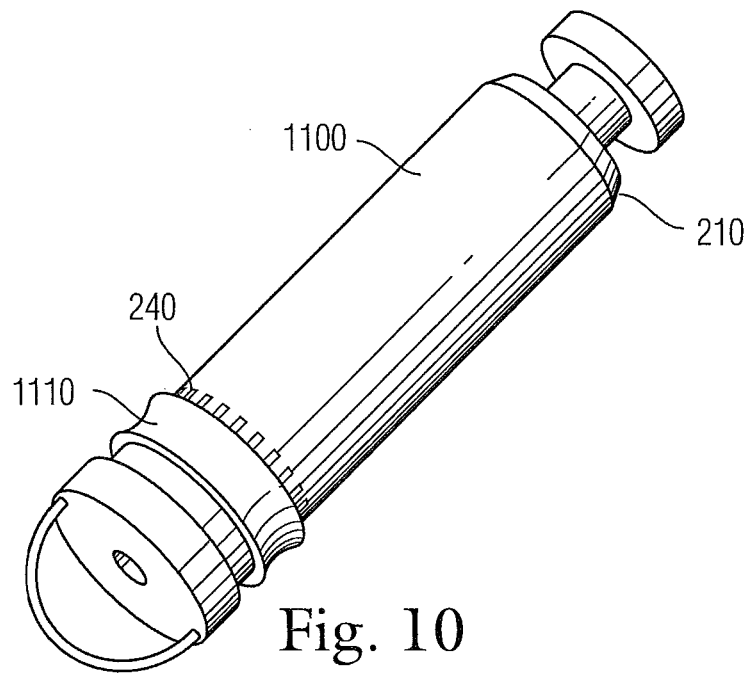
FIG. 10 is a perspective view of a sampling tool according to another embodiment.

FIG. 10 is a side perspective view of a sampling cylinder 1100 according to another embodiment that is similar to the previous embodiments. The difference between the sampling cylinder 1100 and the cylinder 1100 is that the cylinder 1100 includes a different (additional) type of gripping feature and in particular, the cylinder 1100 includes a finger socket band 1110 that extends about a section of the outer surface of the cylinder 1100. The finger socket band 1110 is disposed about the cylinder 1100 proximate an end 1102 of the cylinder 1100 that is spaced from the cutting element 210. The finger socket band 1110, as shown, can be in the form of an elastic band that extends about the circumference of the cylinder 1100. The finger socket band 1110 can be formed so that it has a concave shape including a U or V-shape so long as the user can at least partially insert a finger/thumb within the center recess of the band 1110 to grip and hold the cylinder 1100 during use. Since the finger socket band 1110 is intended to be a gripping surface by which the user holds the cylinder 1100, the finger socket band 1110 can provide a gripping surface that is different from the surrounding surfaces. For example, the finger socket band 1110 can have a roughened/contoured outer surface formed by ribs or the like so as to provide a grip surface that allows the user to more easily hold the cylinder. The cylinder 1100 can be formed of a metal and the finger socket band 1110 can be formed of a rubber or polymeric material. FIG. 12 shows the band 1110 being disposed about the ribs 240 that are part of the outer surface of the cylinder so as to define a gripping zone or region.

Figure 11:
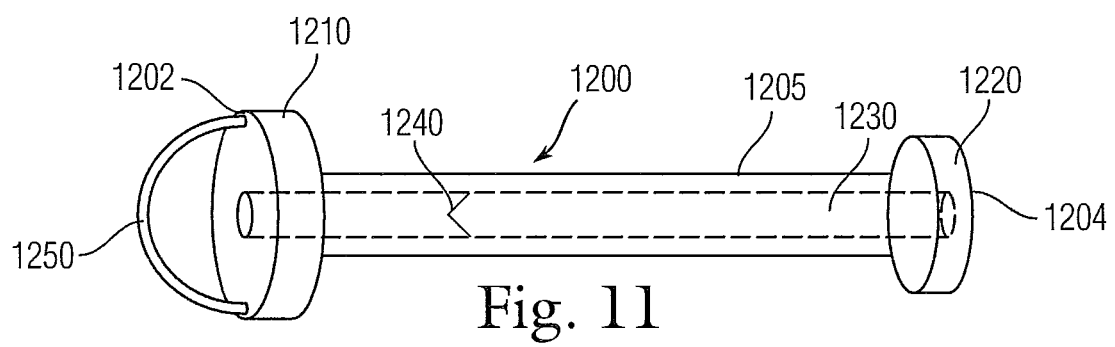
FIG. 11 is a perspective view of a plunger of the sampling tool of FIG. 10.

FIG. 11 illustrates a plunger 1200 according to a different embodiment for use with the sampling tool of the present invention. The plunger 1200 is similar to the plungers previously described herein; however, it contains a different construction. In this embodiment, the central or middle section 1205 of the plunger 1200 has a narrow body compared to the two ends of the plunger 1200. More specifically, the plunger 1200 has a first end 1202 and an opposing second end 1204 with the body of the plunger 1200 extending therebetween. The first end 1202 has an enlarged diameter in that it is defined by a first annular flange (disk) 1210. Similarly, the second end 1204 has an enlarged diameter that is defined by a second annular flange (disk 1220) that seals with the inner wall of the sampling cylinder of the sampling tool to permit a vacuum to be created therein as discussed hereinbefore.

It will be appreciated that one or both of the first and second annular flanges 1210, 1220 can be in the form of O-rings or the like or at least are members that have peripheral edges that can sealingly contact the inner surface of the cylinder. Between the first and second annular flanges 1210, 1220, the plunger body has a cylindrical shape but has a reduced diameter compared to the flanges 1210, 1220 and therefore, the central section 1205 of the plunger 1200 does not contact the inner wall of the cylinder.

As in the other previous embodiments, the plunger 1200 has a central vent feature defined by a vent passage 1230 that extends from and is open at both the fist end 1202 and the second end 1204. The vent passage 1230 thus resembles a central bore that extends through the first flange 1210, the middle section 1205 and the second flange 1220. As shown in the figure, the plunger 1200 can be thought of as having an I-shape.

In accordance with this embodiment, the vent passage 1230 can include a valve 1240 that is located within the vent passage 1230 along its length. For example, the valve 1240 can be located within the vent passage 1230 within the middle section 1205. The valve 1240 can be of the type that permits fluid flow when certain conditions are met. In particular, the valve 1240 is designed to seal off the air producing the desired suction (negative pressure) within the vent passage 1230 that is used to produce at least a partial vacuum formed between the second end 1204 (second flange 1220) and the tissue. The valve 1240 can be manually actuated so as to form the desired vacuum within the vent passage 1230 as the plunger is distracted from the surgical site.

The plunger 1200 also includes a means that permits the extraction of the plunger 1200 from the corresponding cylinder. For example, a handle or member 1250 that can be grasped by a user (technician) is provided at the first flange 1210. In the illustrated embodiment, the handle 1250 is in the form of a wire handle or the like that has a U-shape or semi-circular shape and permits the user to grasp and hold the plunger 1200 by the handle 1250.

Figure 13:
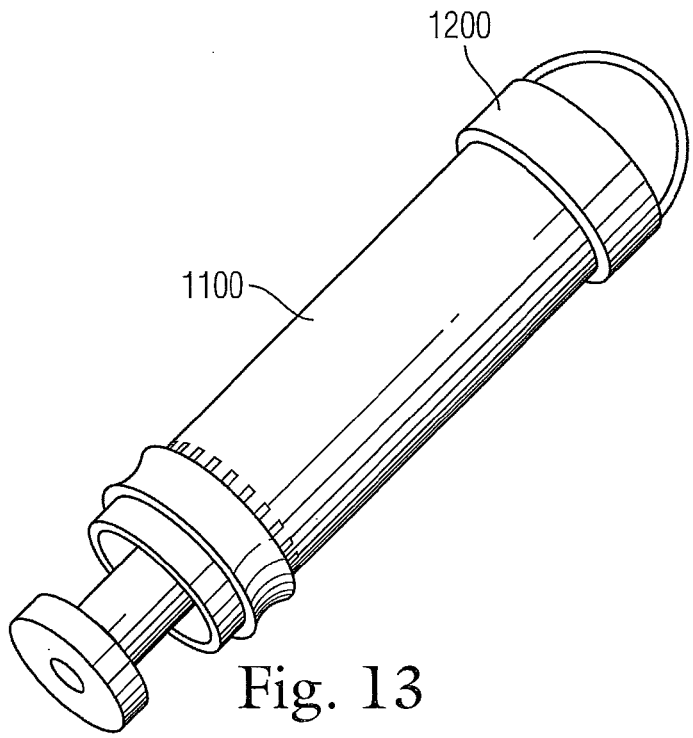
FIG. 13 is a perspective view of the sampling tool arranged for shipping by protecting a cutting blade of the sampling cylinder.
Figure 14:
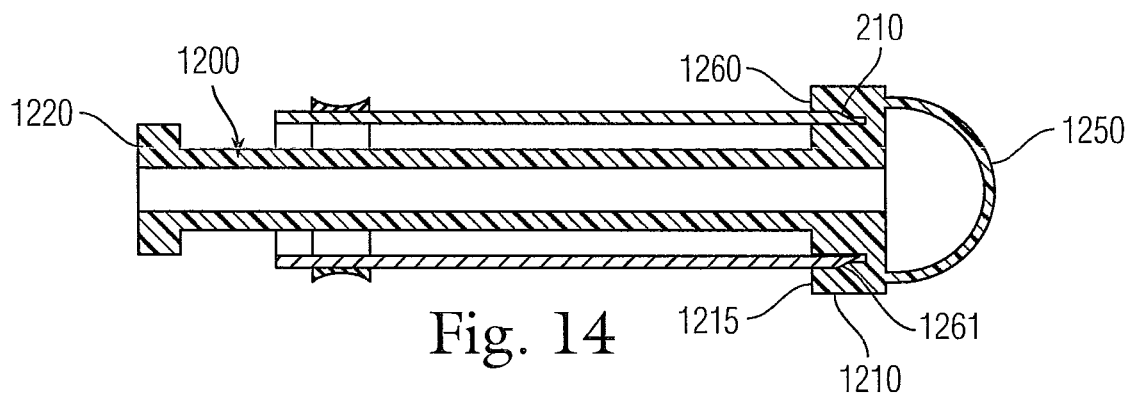
FIG. 14 is a cross-sectional view of the sampling tool of FIG. 13.
Figure 15:
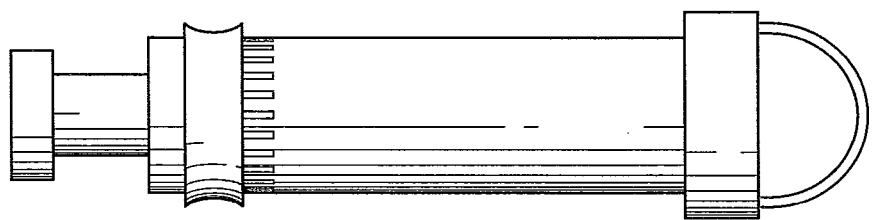
FIG. 15 is a side elevation view of the sampling tool in the shipping position.

Now turning to FIGS. 13-15, in yet another embodiment of the present invention, the sampling tool of the present invention includes a safety feature that permits the blade portion of the sampling cylinder to be securely contained and not accessible during transportation or other handling, thereby preventing accidental pricks or cuts due to the exposed sharp cutting blade coming into contact with a person, etc.

In FIG. 13, the plunger 1200 and sampling cylinder 1100 are shown; however, it will be appreciated that the safety feature can be incorporated into the other plunger constructions described herein. More specifically, the sampling tool is sold and/or transported with the plunger 1200 inserted into the sampling cylinder 1100 from the cutting side. In order to protect the user from an accidental cut produced by the sharp blade, the plunger 1200 is inserted into the sampling cylinder 1100 and the blade 210 is received within a protective slot (channel) 1260 that is formed in the plunger 1200. More specifically, in the case of the plunger 1200, the first flange 1210 can be formed so that it has an enlarged diameter relative to the second flange 1220. The diameter of the first flange 1210 is selected such that it is greater than the diameter of the sampling cylinder 1100 and therefore, the first flange 1210 extends radially outward from and relative to the sampling cylinder 1100. The first flange 1210 has an underside surface 1215 that represents a bottom surface of the first flange 1210 that faces the second flange 1220. Within the underside surface 1215, the blade receiving slot or channel 1260 is formed and is complementary to the blade 210 of the sampling cylinder 1100 in that the blade 210 is able to fit within and be frictionally held within the slot 1260. When the blade 210 is fully inserted into the channel 1260, the blade 210 is not accessible and therefore, accidental injuries are avoided.

In the embodiment, wherein the blade 210 has an annular shape, the channel 1260 is also annular in shape. When the blade does not go completely about the end of the plunger 1200, the channel 1260 similarly does not have to be a continuous circular shaped channel but instead can be a channel having a length that can receive the blade. The blade 210 is frictionally held within the channel 1260 to prevent the sampling cylinder 200 and plunger 1200 from being freely separated. The depth of the channel 1260 is such that when the blade 210 is inserted into the channel 1260, the blade 210 is covered, thereby protecting the user (technician).

In another embodiment, the channel 1260 can be opened and closed by manipulation by the technician such that during normal usage of the sampling tool as a procedure is performed, the channel 1260 remains closed and therefore the opposite end of the cylinder 1100 does not travel within the channel 1260 when the plunger 1200 is directed forward and the underside surface 1215 of the plunger 1200 contacts the opposite end. For example, the slide tab can be moved into at least a portion of the channel 1260 so as to obstruct the channel 1217 and prevent the plunger 1200 from entering the channel 1260. The slide tab extends through a slot formed in the side (exterior) of the first flange 1210 and is accessible by the technician and can be moved within the slot so as to bring at least a portion of the slide tab into the channel 1260. In other words, the slide tab can move freely in and out relative to the first flange 1210. It will be appreciated that any other types of interference creating members can be used so as to at least partially obscure the channel 1260.

In addition, as shown in FIG. 14, the channel 1260 can have a beveled edge 1261 that is complementary to the beveled nature of the cutting blade and therefore, when the blade 210 is inserted fully into the channel 1260, the extent of travel of the blade 210 in the channel 1260 is limited by contact between the blade 210 with the beveled edge of the channel 1260. The beveled edge can thus act as a stop. As shown in FIG. 14, when the blade 210 is in the most forward position and rests against the beveled edge, a small space is present between the blade 210 and the underside surface 1215 so as to protect the sharp blade 210.

Figure 16:
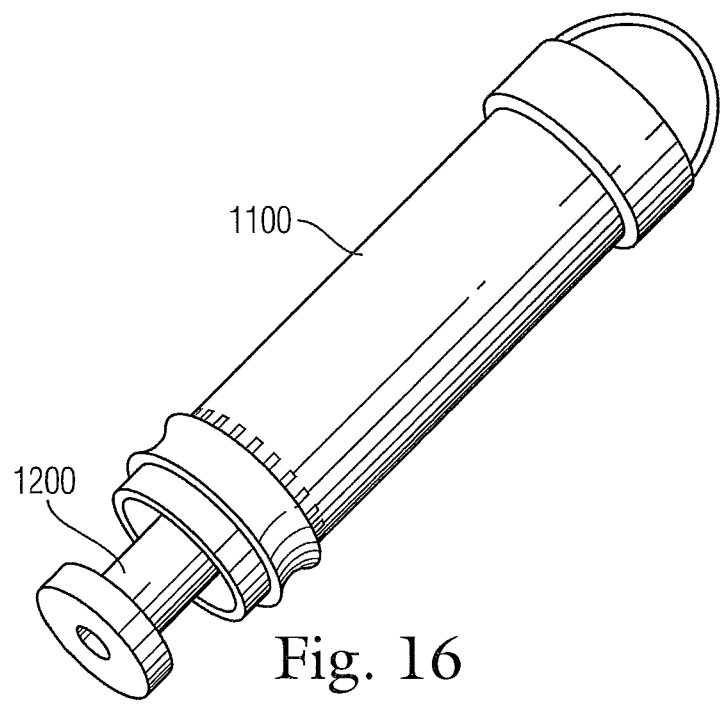
FIG. 16 is a perspective view of the sampling tool arranged for shipping by protecting a cutting blade of the sampling cylinder using another technique.
Figure 17:
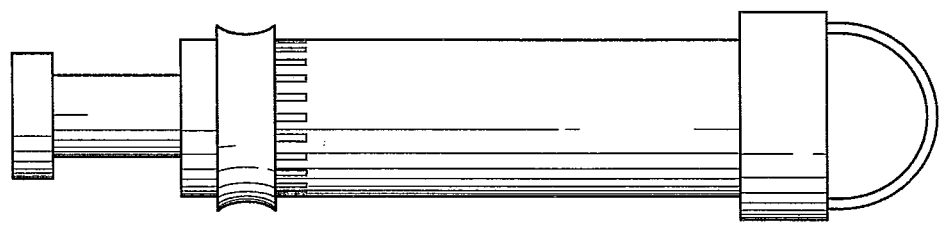
FIG. 17 is a side elevation view of the sampling tool in the shipping position.
Figure 18:
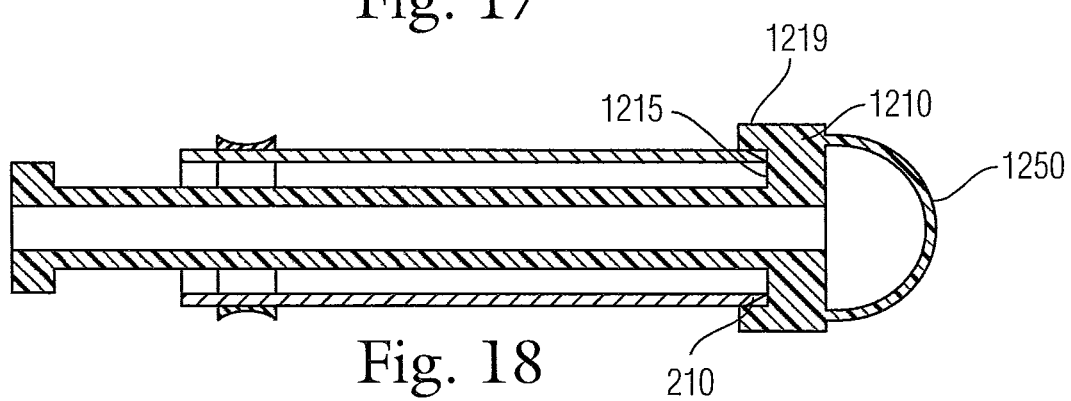
FIG. 18 is a cross-sectional view of the sampling tool of FIG. 16.
Figure 19:
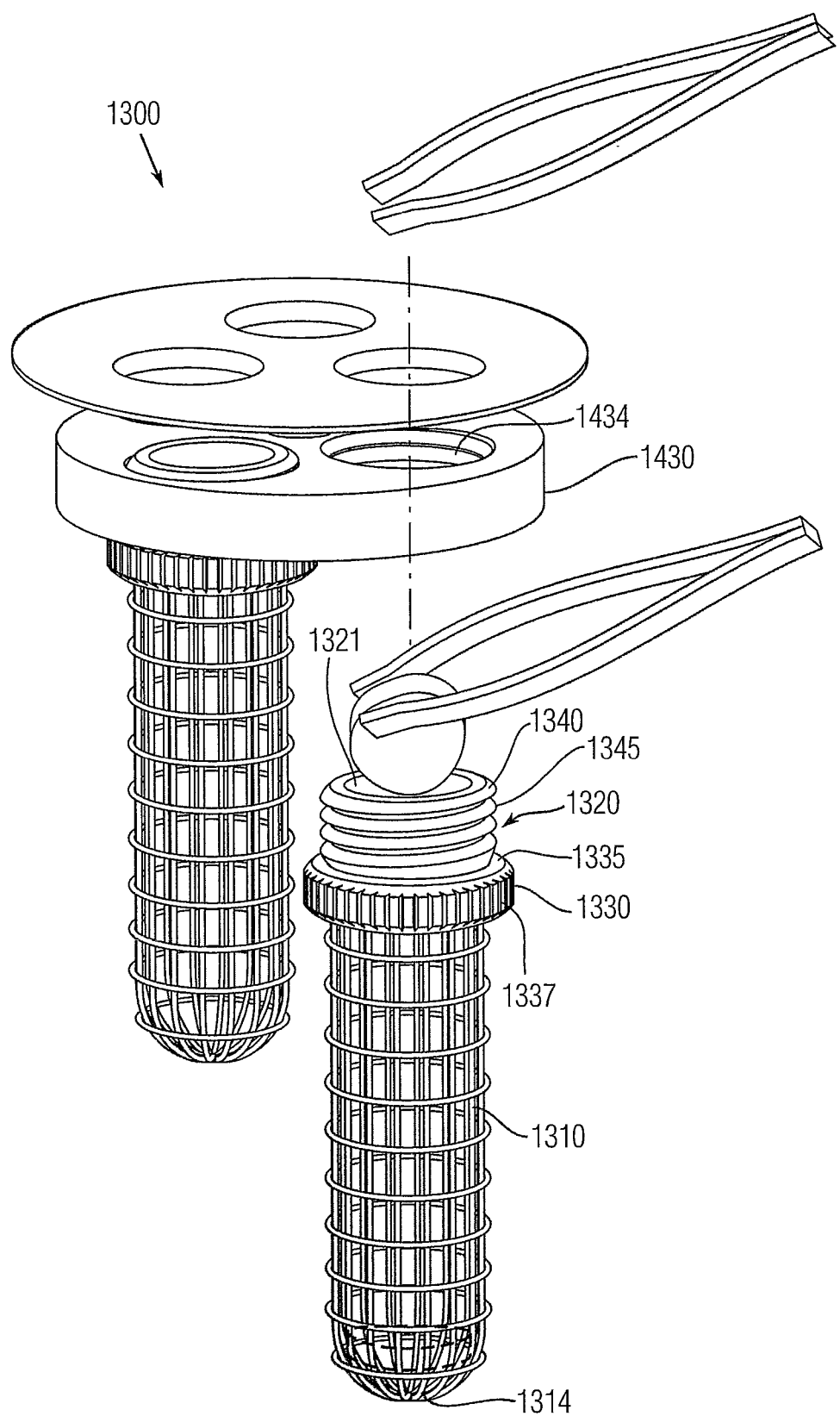
FIG. 19 is a perspective view of a wire-mesh tube assembly for use with a washing jar accessory.

In yet another embodiment shown in FIGS. 16-18, the plunger can have a blade shield 1219 that blocks free access to the blade 210 of the cylinder 200. For example, in the case of the plunger 1200, the first flange 1210 can have a downwardly extending flange or blade shield 1219 (annular shaped lip) that extends from the underside surface 1215. When the blade 210 contacts the underside surface 1215 in the shipped or transported position, the blade shield 1219 is disposed adjacent the blade 210 so as to protectively cover the blade 210. A frictional fit is provided between the sampling cylinder 200 and the plunger 1200 resulting in the plunger being held in this shipping position.

FIGS. 19-22 show a wire-mesh tube assembly 1300 for holding a biopsy specimen. The wire-mesh tube assembly 1300 includes a wire-mesh tube 1310 that is of a size for receiving and holding the biopsy specimen. The wire-mesh tube 1310 has an open end 1312 and an opposite closed end 1314. The wire-mesh tube 1310 includes circular shaped rings 1313 that are located in series along the length of the tube 1310 and surround the longitudinally extending wires 1315 that extend the length of the tube 1310. The tube 1310 is formed such that there the wires 1315 have free ends 1319 that extend beyond the last ring 1313 closest to the open end 1312.

The assembly 1300 further includes a cap 1320 that mates with the wire-mesh tube 1310. The cap 1320 is a threaded member and includes a first section 1330 and a second section 1340. The first section 1330 is formed at one end of the cap 1320, while the second section 1340 is formed at the other end of the cap 1320. The diameter (width) of the first section 1330 is greater than the diameter of the second section 1340 and therefore protrudes radially outward therefrom. A shoulder and ledge 1335 are formed between the first and second sections 1330, 1340. The height of the second section 1340 can be greater than the height of the first section 1330.

Each of the first and second sections 1330, 1340 is an annular shaped member (concentric members). Along an exterior (peripheral) surface of the second section 1340, threads 1345 are formed (helically shaped threads). The threads 1345 permit the assembly 1300 to be threadingly fastened (screwed) into another member, such as a part of the accessory jar cap. Along an exterior (peripheral) surface of the first section 1330, a plurality of teeth 1337 are formed and extend circumferentially about the first section 1330. The teeth 1337 provides improved gripping and allows the user to easily rotate the assembly 1300.

The cap 1320 can be a hollow member with a through hole 1321 formed centrally therein. The through hole 1321 can have a uniform diameter from one end to the other end. In other words, the through hole is formed uniformly through the first section 1330 and the second section 1340. The diameter of the through hole 1321 is selected to allow the wire-mesh tube 1310 to be received within and retiringly coupled to the cap 1320. The open end 1312 of the wire-mesh tube 1310 is inserted into the through hole 1321 at the first section 1330 and is then coupled to the cap 1320. When the cap 1320 is attached to the wire-mesh tube 1310, the interior of the wire-mesh tube 1310 is accessible through the through hole 1321 formed in the cap 1320.

The wire-mesh tube 1310 can be attached to the cap 1320 by any number of different techniques, including providing a frictional fit therebetween. For example, the free ends 1319 that extend beyond the last ring 1313 can be received with small openings 1329 formed along an annular ledge or platform that is located within the through hole 1321 of the cap 1320 (and formed in the first section 1330 of the cap 1320). This results in a frictional fit between the wire-mesh tube 1310 and the cap 1320. Alternatively, the tube 1310 can be frictionally held within the cap 1320 by seating against the inner wall thereof (e.g., seating against a shoulder formed therein).

Figure 20:
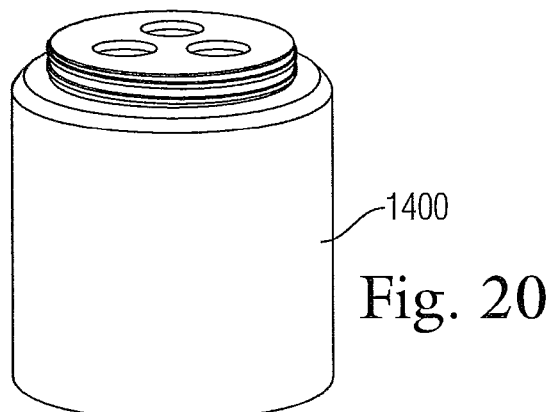
FIG. 20 is a perspective view of the wire-mesh tube assembly fitted on top of the washing jar.
Figure 21:
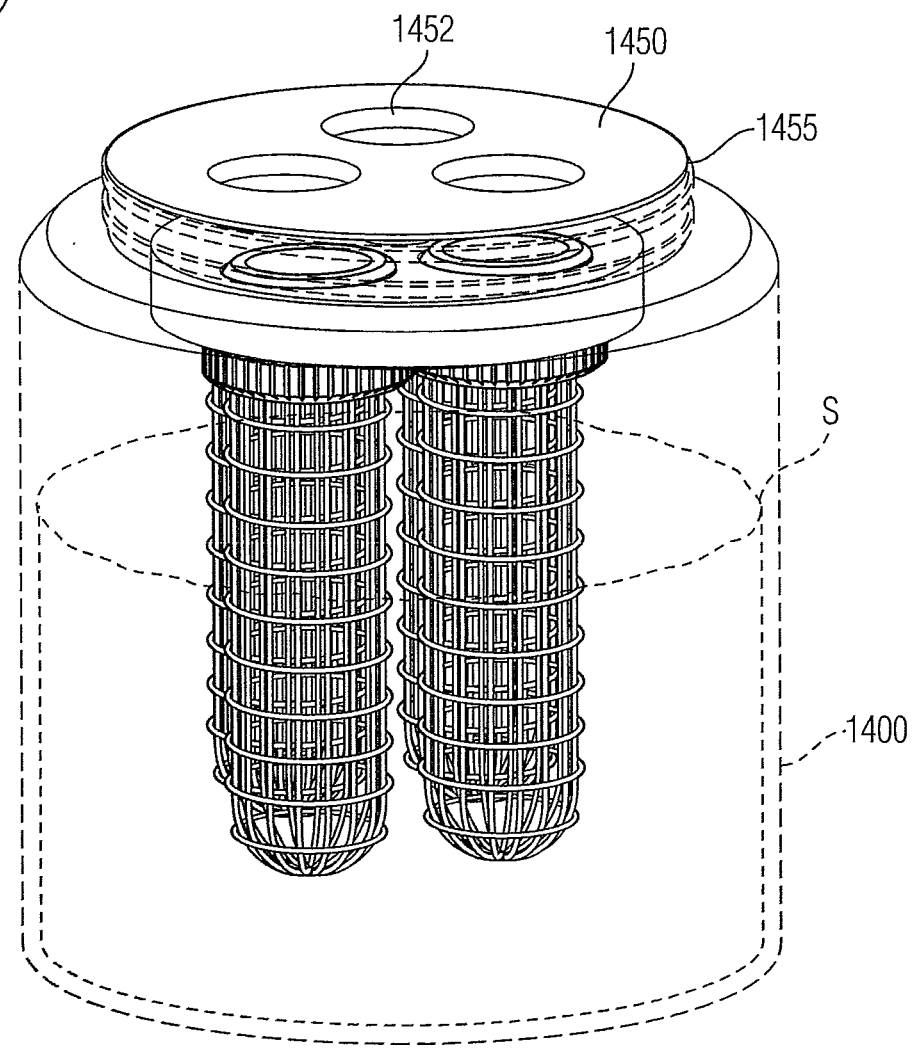
FIG. 21 is a side perspective view of the wire-mesh tube assembly fitted on top of the washing jar showing the interior thereof.
Figure 22:
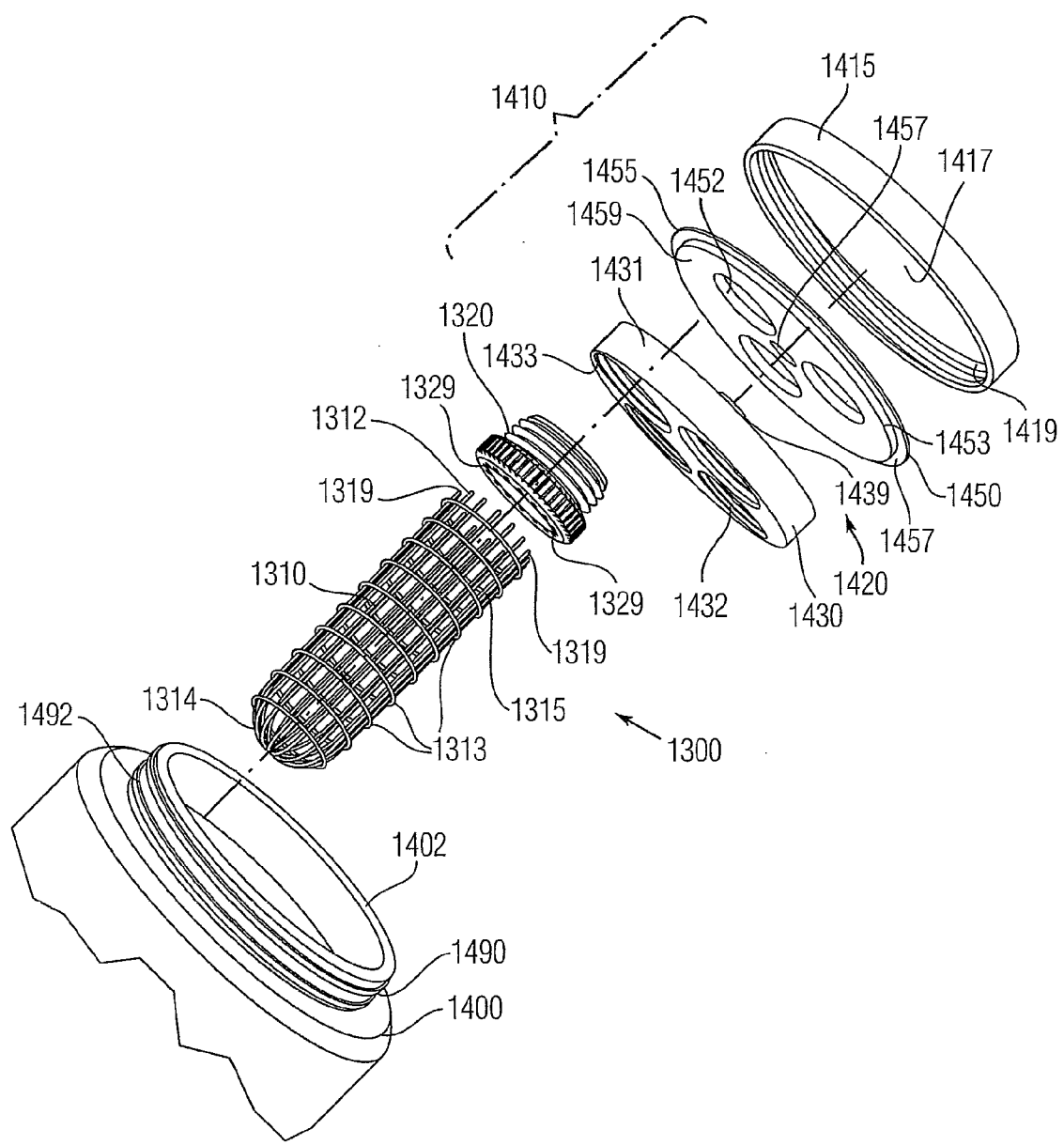
FIG. 22 is an exploded perspective view of the wire-mesh tube assembly.
Figure 23:
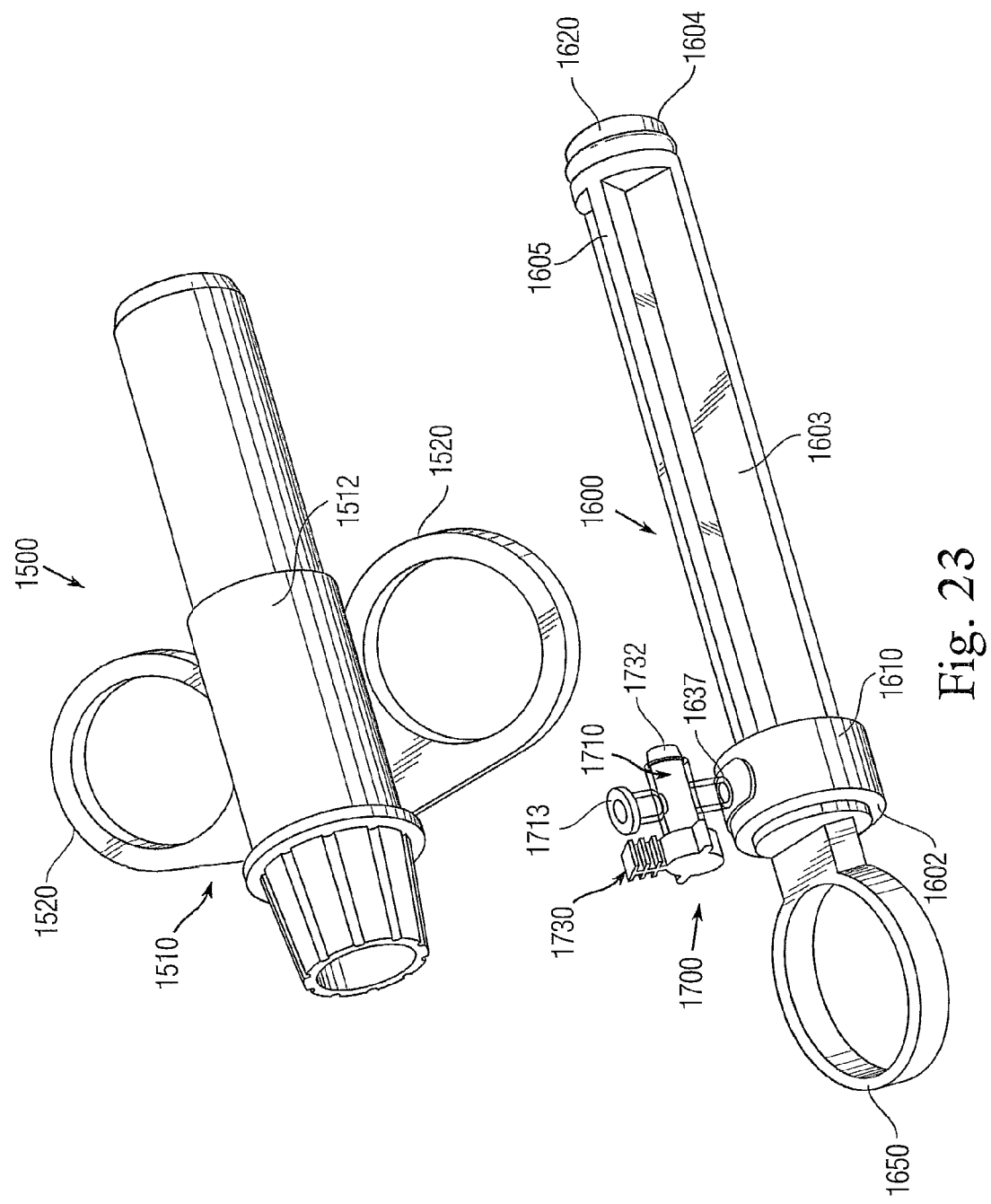
FIG. 23 is an exploded perspective view of a sampling cylinder and a plunger of a sampling tool according to another embodiment.
Figure 24:
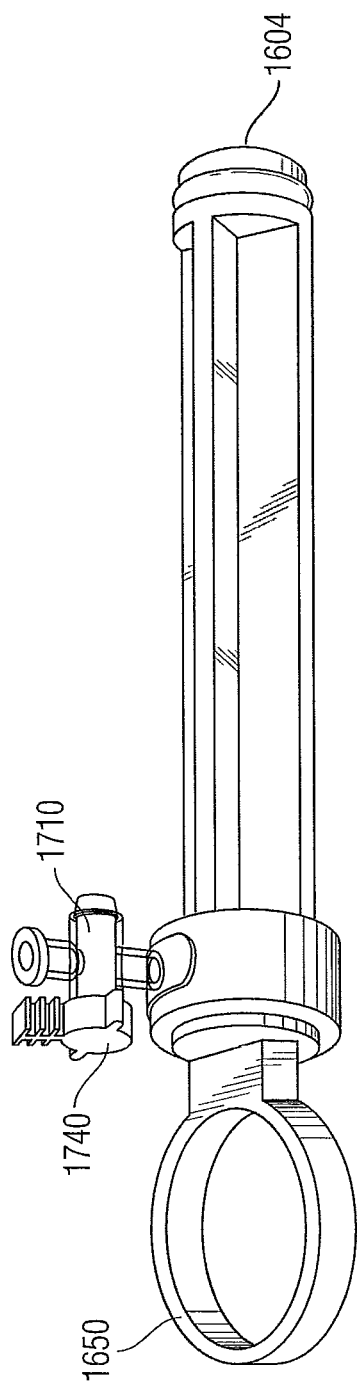
FIG. 24 is an exploded perspective view of a plunger according to one embodiment with an air vent valve being in an open position.

FIGS. 20-22 show how the wire-mesh tube assembly 1300 mates with a collection container 1400, such as a biopsy collection jar. The container 1400 can be in the form of a hollow container (e.g., plastic or glass) that permits reception of items through an open end 1402 that is opposite the closed end 1404 of the container 1400. The container 1400 includes a cap assembly 1410 for covering an open end 1402 of the container 1400. The cap assembly 1410 includes an outer cover 1415 that has an inner surface 1417. The outer cover 1415 typically has a circular shape; however, other shapes are possible. Threads 1419 can be formed within the outer cover 1415 along an inner side wall thereof.

The cap assembly 1410 includes a tube coupling interface 1420 that interfaces between the wire-mesh tube assembly 1300 and the outer cover 1415. The interface 1420 includes a coupling or support member 1430 that is constructed to mate with the individual wire-mesh tube assemblies 1300. For example, the coupling member 1430 can be a disk-shaped member that includes through openings 1432 formed therein and spaced apart from one another. Each through opening 1432 is in the form of a threaded opening that includes threads 1434 that are complementary to the threads 1345 and therefore, the joined cap 1320/wire-mesh tube 1310 can be securely and threadingly attached to the coupling member 1430 by inserting the threaded second section 1340 within the threaded opening 1432 and turning one member relative to the other.

The formation of multiple threaded openings 1432 in the coupling member 1430 permit a plurality of wire-mesh tube assemblies 1300 to be attached thereto (each assembly 1300 is mated to one threaded opening 1432). In the illustrated embodiment, there are four wire-mesh tube assemblies 1300 that are attached to the coupling member 1430.

When the wire-mesh tube assemblies 1300 mate with the coupling member 1430, the tube assemblies 1300 are placed in an upstanding orientation adjacent one another. The wire-mesh tube assemblies 1300 are still accessible through the openings 1432 formed in the coupling member 1430.

Any number of different means can be used to attach the wire-mesh tube assemblies 1300 to the coupling member 1430. For example, a top surface 1431 of the coupling member 1430 that is opposite a bottom surface 1433 from which the wire-mesh tube assemblies 1300 depend can have a central post 1439 that is located centrally between the through openings 1432.

The cap assembly 1410 also includes a plate 1450 that provides an interface between the coupling (support) member 1430 and the outer cover 1415 and also serves to position and suspend and support the cap assembly 1410 over the collection jar. The plate 1450 can be a disk-shaped structure and includes a plurality of openings 1452 formed therein. The number of openings 1452 can be different than the number of openings 1432 formed in the coupling member 1430 and in particular, the number of openings 1452 is less than the number of openings 1432. In the illustrated embodiment, there are three openings 1452 compared to four openings 1432.

The plate 1450 includes a recess or depression 1457 that is formed the bottom surface from the plate 1450 that faces the coupling member 1430. The recess 1457 receives the central post 1439 of the coupling member 1430 so as to permit the coupling member 1430 to be attached to the plate 1450 as by a mechanical attachment (frictional fit). The illustrated central recess 1457 and the post 1439 have circular shapes and thus, even when the two are mated and attached to one another, one part can optionally rotate relative to one another. As described below, this permits the degree of registration, if any, between the openings 1452, 1432 to be varied if desired. Alternatively, the plate 1450 can mate to the coupling member 1430 such that rotation between the two is prevented.

It will also be understood that the locations of the mating recess and post can be reversed in that the underside or bottom surface of the plate 1450 can include a downwardly extending post formed between the openings 1452 and a top surface of the coupling member 1430 can include a central recess formed between the openings 1432 that receives the post of the plate 1450.

The plate 1450 is positioned on the top of the rack to permit a user to grasp and hold the whole rack while emptying the jar between washes and to unscrew one wire mesh tube at the time in order to recover each biopsy from the tube and complete the tissue processing and storage.

The plate 1450 has a stepped construction in which an annular shoulder 1453 is formed proximate a peripheral edge 1455 of the plate 1450 so as to define a central platform 1459. The central platform 1459 has the same or substantially the same dimensions (width) of the coupling member 1430 so that when the two mate together, the peripheral edges of each overlie one another with the peripheral edge 1455 extending radially outward therefrom. A ledge 1457 is formed between the shoulder 1453 and the peripheral edge 1455. The formation of the shoulder 1453 and the ledge 1457 provides a means for positioning the plate 1450 and the joined structure relative to the collection jar 1400.

The ledge 1457 is designed to seat against the top edge 1402 of the collection jar 1400 and thus suspend the joined coupling member 1430 and wire-mesh tube assemblies 1300 within the interior of the collection jar 1400. The size of the ledge 1457 is such that it does not interfere with the attachment of the outer cover to the collection jar 1400. A neck 1490 of the collection jar 1400 can include external threads 1492 that mate with threads formed on the outer cover to securely attach the two. The top edge 1402 is part of the neck 1490 and represents the top of the jar 1400.

The outer cover 1415 does not include any openings and therefore, when the joined coupling member 1430 and plate 1450 are inserted into the outer cover 1415, access to the wire-mesh tubes is prevented.

As shown in the figures, when the wire-mesh tube assemblies 1300 are mated to the cap assembly 1410, the wire-mesh tubes are at least substantially perpendicularly oriented relative to the outer cover 1415 when it is attached to the jar 1400. The wire-mesh tube assemblies 1300 thus hang from the cap assembly 1410 and the wire-mesh tubes are inserted into the interior of the collection jar 1400. The interior of the collection jar 1400 is sized so that when the outer cover 1415 mates with the collection jar 1400, the wire-mesh tube assemblies 1300 hang within the collection jar 1400 but do not strike the floor (bottom) of the collection jar 1400.

The collection jar 1400 serves as a biopsy washing device and an appropriate solution, such as a saline washing solution (S), is contained within the collection jar. The biopsy specimens that are contained within the wire-mesh tube assemblies 1300 is then subjected to the saline (washing) solution.

It will be appreciated that one or more biopsy tube assembly 1300 can be used with the cap assembly 1410. For example, if only a single biopsy is collected, only one tube assembly 1300 can be coupled to the cap assembly 1410. However, as mentioned previously, in placenta sampling, four biopsies are typically collected and therefore, the cap assembly 1410 can be used to hold and maintain the four biopsies in the cleaning solution within the jar.

Since the plate 1450 can be rotated relative to the coupling member 1430 and vice versa and there are less openings 1452 compared to openings 1432, the degree of openness of the tube assembly 1300 can be varied. In particular, one opening 1452 can be placed in complete registration with the opening 1432 resulting in the tube assembly 1300 being completely open. Alternatively, the openings 1452 of the plate 1450 can be offset from one opening 1432 thereby resulting in the tube assembly 1300 being completely closed. In addition, the opening 1452 can be placed in partial registration with the opening 1432 such that the tube assembly 1300 is partially open (e.g., a crescent shaped opening can be provided due to the registration between the openings 1452, 1432).

It will therefore be appreciated that the sampling tools described herein allow easy isolation of cylindrical core tissue biopsies (e.g., placental biopsies) of a replicated size that can be used for multiple downstream applications. The present sampling tools overcome the disadvantages that are associated with the conventional tools described herein. It should also be appreciated that the sampling tools of the present invention are not operated as in a conventional punch tool since a forward advancement of the cutting implement (blade) into placenta will not result in a discrete, nicely defined core sample being isolated and collected due to the nature of the placenta as discussed herein.

In addition, the cutting implement (cutting blade) can have a different form in that the cutting implement can be a serrated blade (e.g., the blade can have an undulating cutting surface). The blade can also be treated (modified) to enhance and optimize the cutting of tissue. For example, a surface coating (e.g., a diamond coating) can be applied to the blade.

It will be appreciated that the sampling tool and one or more accessories can be distributed in a kit form.

Now referring to FIGS. 23-27, FIG. 23 is a side perspective view of a sampling cylinder 1500 according to another embodiment that is similar to the previous embodiments. The difference between the sampling cylinder 1500 and the other cylinders disclosed herein is that the cylinder 1500 includes a different (additional) type of gripping feature and in particular, the cylinder 1500 includes a finger holder 1510 that mates with the cylinder 1500. The finger holder 1510 can be integrally formed with the cylinder 1500 or the finger holder 1510 can be a separate part that is mated to one end of the cylinder 1500. The finger holder 1510 can be formed of a different material relative to the cylinder 1500. For example, the finger holder 1510 can be formed of a plastic material, while the cylinder 1500 is metal.

The finger holder 1510 includes a main portion 1512 that is hollow and receives the end of the cylinder 1500. The main portion 1512 can thus have a round hollow interior since the cylinder 1500 has a cylindrical shape. The main portion 1512 can include an internal shoulder that limits the degree of travel of the cylinder 1500 within the finger holder 1510. The finger holder 1510 includes a pair of finger loops 1520 that protrude outwardly from the finger holder 1510. The loops 1520 are intended to receive a finger or thumb and permit a user to hold the cylinder 1500 during use.

FIGS. 24-27 show a plunger 1600 according to a different embodiment for use with the sampling cylinder 1500 of the present invention. The plunger 1600 is similar to the plungers previously described herein; however, it contains a different construction. In this embodiment, the central or middle section 1603 of the plunger 1600 is formed of longitudinal reinforcing ribs 1605 (e.g., 4 ribs arranged 90 degrees apart from one another). More specifically, the plunger 1600 has a first end 1602 and an opposing second end 1604 with the body of the plunger 1600 extending therebetween. The first end 1602 has an enlarged diameter in that it is defined by a first annular flange (disk) 1610. Similarly, the second end 1604 has an enlarged diameter that is defined by a second annular flange (disk 1620) that seals with the inner wall of the sampling cylinder of the sampling tool to permit a vacuum to be created therein as discussed hereinbefore.

As in the other previous embodiments, the plunger 1600 has a central vent feature defined by a vent passage 1630 that extends from and is open at the second end 1604. The vent passage 1630 includes a main section 1631 that resembles a central bore that extends through the second flange 1620 and the middle section of the plunger 1600. The first flange 1610 also includes a second portion of the vent passage 1630 in that the other open end of the vent passage 1630 is formed along a side of the first flange 1610. As shown in FIGS. 26-27, a second section 1635 is formed in the first flange 1610 and is in communication with the main section 1631 of the vent passage 1630 and is open at a point 1637 along the side wall of the first flange 1610. In the illustrated embodiment, the vent passage section 1635 and the main section 1631 are formed at a right angle; however, this is merely exemplary in nature and it can be formed at other angles relative to the main section 1631.

The plunger 1600 includes a controllable valve mechanism 1700 that permits the user to either open or close the vent passage 1630 to atmosphere. In other words, when in the open position, the vent passage 1630 (formed of sections 1631 and 1635) is open from the end 1604 to the point 1637. The valve mechanism 1700 is disposed along the side wall of the flange 1610 and extends outwardly thereof. The valve mechanism 1700 includes a main valve section 1710 that has a center bore 1712 that is in communication with the section 1635 and permits the section 1635 to be open to atmosphere.

The main valve section 1710 can be formed as a plastic part that is attached to or is integrally formed with the flange 1610. The main valve section 1710 further includes a side extension 1720 that extends outwardly from the main valve section 1710 and is hollow so as to define a hollow space. In the illustrated embodiment, the side extension 1720 is formed at an intermediate location of the main valve section 1710 between a distal end 1713 and the side wall of the flange 1610. The side extension 1720 can be formed at a right angle to the main valve section 1710. The hollow interior of the side extension 1720 thus intersects the hollow interior of the main valve section 1710. The distal end 1713 of the valve section 1710 can include a connector feature, such as an enlarged flange, to allow the valve section 1710 to be attached to some other device via tubing or the like.

The valve mechanism 1700 includes an adjustable valve control member 1730 that is disposed within the hollow interior of the side extension 1720 and is movable therein. The control member 1730 can thus include a first leg 1732 that is sized and shaped to be sealingly received within the hollow interior of the side extension 1720. The first leg 1732 includes a second through bore 1735 (through hole) that passes therethrough. The bore 1735 can be shaped and sized based on the hollow interior of the main valve section 1710. In other words, the bore 1735 can be a cylindrical shaped hole that has approximately the same diameter as the diameter of the hollow channel (bore) 1712 formed in the main valve section 1710. The control member 1730 includes another leg 1740 that represents a handle that can be grasped by a user and permits the user to rotate the first leg 1732 within the hollow interior space of the side extension 1720. For example, the first leg 1732 can be cylindrically shaped and can rotate within the side extension 1720 so as to position the bore 1735 relative to the bore in the main valve section 1710.

Figure 25:
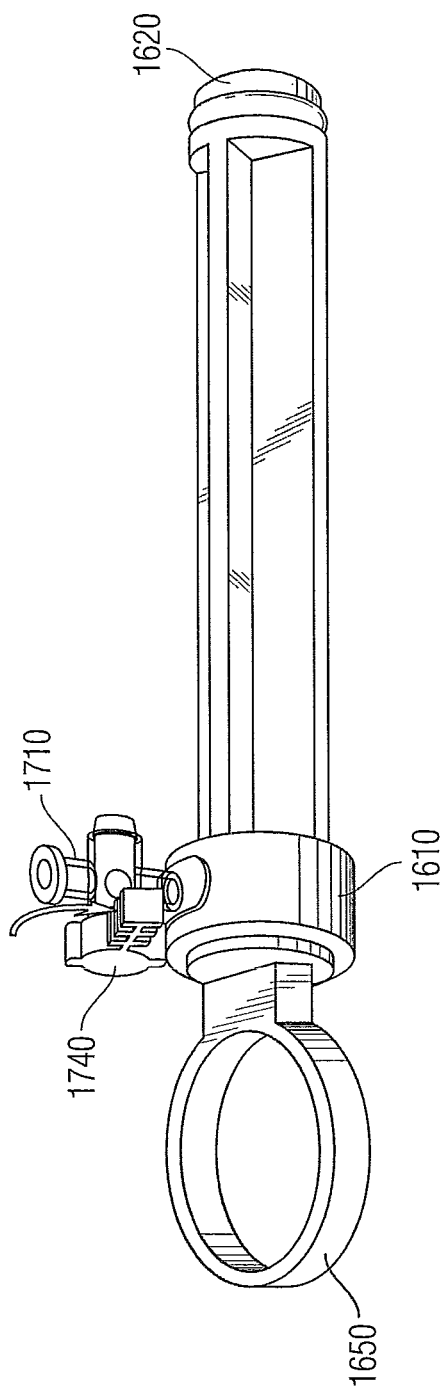
FIG. 25 is an exploded perspective view the plunger with the air vent valve being in the closed position.

In other words, to place the valve mechanism 1700 in the open position, the control member 1730 is rotated so as to position the bore 1735 in alignment (registration) with the bore of the main valve section 1710 as shown in FIG. 26. Conversely, to place the valve mechanism 1700 in the closed position, the control member 1730 is rotated so as to position the bore 1735 out of registration with the bore in the main valve section 1710. Rotation is shown in FIG. 25 where the control member 1730 is rotated 90 degrees from the position in FIG. 24 which is a fully opened position.

It will be understood that as the control member 1730 is rotated, different degrees of registration between the bore 1735 and the bore in the main valve section 1710 result.

In particular, the valve mechanism 1700 is designed to seal off the air producing the desired suction (negative pressure) within the vent passage that is used to produce at least a partial vacuum formed between the second end 1604 (second flange 1620) and the tissue. The valve mechanism 1700 can thus be manually actuated so as to form the desired vacuum within the vent passage as the plunger is distracted from the surgical site.

The plunger 1600 also includes a means that permits the extraction of the plunger 1600 from the corresponding cylinder. For example, a handle or member 1650 that can be grasped by a user (technician) is provided at the first flange 1610. In the illustrated embodiment, the handle 1650 is in the form of a wire handle or the like that has a U-shape or semi-circular shape and permits the user to grasp and hold the plunger 1600 by the handle 1650.

While the invention has been described in connection with certain embodiments thereof, the invention is capable of being practiced in other forms and using other materials and structures. Accordingly, the invention is defined by the recitations in the claims appended hereto and equivalents thereof.

What is claimed is:

1. A sampling tool for isolating and collecting a tissue sample comprising:
   a hollow sampling cylinder that includes a first end and an opposing second end, the first end comprising a sharpened, circular cutting edge, wherein the hollow sampling cylinder includes a central bore extending completely from the first end to the second end, wherein an outer surface of the sampling cylinder includes a modified gripping surface; and
   a plunger having a first end and a second end, the plunger being slidingly received within the hollow sampling cylinder and movable to a fully inserted position relative to the hollow sampling cylinder, the plunger including a shaft portion that terminates in the first end of the plunger, the plunger having a handle portion at the second end of the plunger, wherein the handle portion has greater dimensions than the shaft portion, wherein the first end of the plunger comprises a planar surface for contacting the tissue sample, wherein an outer surface of the shaft portion is in contact with an inner wall of the hollow sampling cylinder that defines the central bore, wherein the plunger includes at least one air evacuation feature constituted by a continuous channel formed through the plunger and extending from the first to second end of the plunger, the air evacuation feature being open at both the first and second ends of the plunger including being open along the planar surface at the first end of the plunger which defines a distalmost face of the plunger, wherein the planar face of the plunger comprises a distalmost structure of the sampling tool when the plunger is in the fully inserted position relative to the hollow sampling cylinder.

2. The sampling tool of claim 1, wherein the sampling cylinder has a length of at least about 7.5 cm and a diameter of at least about 1.5 cm.

3. The sampling tool of claim 1, wherein the bore has a cylindrical shape to isolate and collect a cylindrical core tissue sample.

4. The sampling tool of claim 1, wherein the sampling cylinder and plunger are configured to cut and collect placental tissue.

5. The sampling tool of claim 1, wherein the continuous channel is formed centrally within the plunger.

6. The sampling tool of claim 1, wherein the sampling cylinder comprises a hollow plastic tube that includes an annular blade formed in in-situ with a body of the plastic tube, the annular blade defining the cutting edge.

7. The sampling tool of claim 1, wherein the sampling cylinder comprises a hollow plastic tube that includes a linear blade formed at the first end, the linear blade extending less than a complete circumference of the tube.

* * * * *